US008454986B2

(12) United States Patent
De Windt et al.

(10) Patent No.: US 8,454,986 B2
(45) Date of Patent: *Jun. 4, 2013

(54) SILVER NANOPARTICLES WITH SPECIFIC SURFACE AREA AND A METHOD FOR PRODUCING THEM

(75) Inventors: Wim De Windt, Sint-Amandsberg (BE); Mariane Van Wambeke, Kluisbergen (BE); Willy Verstraete, Wondelgem (BE); Nico Boon, Balegem (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/810,320

(22) PCT Filed: Jan. 2, 2009

(86) PCT No.: PCT/EP2009/050019
§ 371 (c)(1),
(2), (4) Date: Jun. 24, 2010

(87) PCT Pub. No.: WO2009/087122
PCT Pub. Date: Jul. 16, 2009

(65) Prior Publication Data
US 2010/0272770 A1    Oct. 28, 2010

(30) Foreign Application Priority Data

Jan. 4, 2008 (GB) .................................. 0800081.2

(51) Int. Cl.
| A01N 25/08 | (2006.01) |
| A01N 59/16 | (2006.01) |
| H01B 1/22  | (2006.01) |
| C12P 3/00  | (2006.01) |
| C22C 5/96  | (2006.01) |
| A01P 1/00  | (2006.01) |

(52) U.S. Cl.
USPC ............ 424/411; 424/618; 424/409; 435/168

(58) Field of Classification Search
USPC ........................... 242/411, 618, 409; 435/168
See application file for complete search history.

(56) References Cited

U.S. PATENT DOCUMENTS

| 6,379,712 B1* | 4/2002 | Yan et al. ........................ 424/618 |
| 2002/0174743 A1 | 11/2002 | Mukherjee et al. |
| 2003/0004375 A1* | 1/2003 | Mizrahi et al. ................. 562/589 |
| 2005/0013759 A1 | 1/2005 | Grow |
| 2007/0207335 A1* | 9/2007 | Karandikar et al. .......... 428/560 |
| 2009/0239280 A1 | 9/2009 | De Windt et al. |

FOREIGN PATENT DOCUMENTS

| DE | 10337399 | 3/2005 |
| JP | 2004/137241 | 5/2004 |
| WO | WO 02/18699 | 3/2002 |
| WO | WO 2008/003522 | 1/2008 |
| WO | WO 2009/087122 | 7/2009 |

OTHER PUBLICATIONS

Nair et al. Coalescence of Nanoclusters and Formation of Submicron Crystallites Assisted by *Lactoballus* Strains. Crystal Growth and Design vol. 2 No. 4 pp. 293-298 (2002).*
Nair et al. Crystal Growth and Design vol. 2, No. 4 293-298, 2002.*
Zheng-yi Journal of Environmental Sciences. vol. 14, No. 1 pp. 141-144, 2002.*
RXmed. LACTAID http://www.rxmed.com/b.main/b2.pharmaceutical/b2.1.monographs/CPS-%20Monographs/CPS-%20(General%20Monographs-%2L)/LACTAID.html.*
Database WPI, Week 200245, Derwent Publications Ltd., London, GB; AN 2002-425694, Accessed Oct. 2007, 2 pages.
Database WPI, Week 200435, Derwent Publications Ltd., London, GB; AN 2004-369133, Accessed Oct. 2007, 2 pages.
Fu et al. "Rapid preparation process of silver nanoparticles by Bioreduction and Their Characterization" Chinese Journal of Chemical Engineering, Chemical Industry Press, Feb. 1, 2006, 14(1), 114-117.
Kashefi et al. "Reductive Precipitation of Gold by Dissimilatory Fe(III)-Reducing Bacteria and Archaea", Applied and Environmental Microbiology, Jul. 2001, 67(7), 3275-3279.
Klaus et al. "Silver-based crystalline nanoparticles, microbially fabricated" Proceedings of the National Academy of Science of USA, Nov. 23, 1999, 96(24), 13611-13614.
Mandal et al. "The use of microorganisms for the formation of metal nanoparticles and their application", Applied Microbiology and Biotechnology, Jan. 2006, 69(5), 485-492.
Merroun et al. "Spectroscopic characterization of gold nanoparticles formed by cells and S-layer of *Bacillus sphaericus* JG-A12", Materials Science and Engineering: C, Jan. 2007, 27(1), 188-192.
Morones et al. "The bactericidal effect of silver nanoparticles; The bactericidal effect of silver nanoparticidal effect of silver nanoparticles" Nanotechnology, Oct. 1, 2005, 16(10), 2346-2353.

(Continued)

*Primary Examiner* — Anoop Singh
*Assistant Examiner* — Anna Falkowitz
(74) *Attorney, Agent, or Firm* — Woodcock Washburn LLP

(57) ABSTRACT

Silver nanoparticles associated with 20 to 80% by weight of a biocomponent of the genus *Lactobacillus*, said silver nanoparticles having a ratio of the average particle size to the specific surface area (BET) of from 0.015 to 0.15 nm/m$^2$/g; a method for producing silver nanoparticles, comprising the step of incubating bacteria of the genus *Lactobacillus* with an aqueous solution comprising at least 4 mM of a silver salt in the presence of ammonia and an alkali metal hydroxide until a biomass of bacteria containing Ag$^0$ silver nanoparticles is formed; and optionally a further step of extracting said Ag$^0$ silver nanoparticles from said biomass by means of concentrated alkali metal hydroxide or concentrated inorganic acid or enzymes; an anti-microbial composition comprising an effective amount of said silver nanoparticles; use of said silver nanoparticles for the manufacturing of an article or a composition with anti-microbial activity; a method for manufacturing an article or a composition with anti-microbial activity, comprising dispersing or impregnating said silver nanoparticles into said article or composition; and an article with anti-microbial property having said silver nanoparticles dispersed therein.

26 Claims, 1 Drawing Sheet

OTHER PUBLICATIONS

Mukherjee et al. "Bioreduction of AuCl$_4$- Ions by the Fungus, *Verticillium* sp. and Surface Trapping of the Gold Nanoparticles Formed", Angewandte Chemie. International Edition, Oct. 2001, 40(19), 3585-3588.

Nair et al. "Coalescence of nanoclusters of submicron crystallites assisted bylactoba strains" Crystal Growth & Design, Jan. 1, 2002, 2(4), 293-298.

Pei et al. "Synthesis of Gold Nanorods by Surfactant-assisted One-step Chemical Reduction Method", Abstracts, 206th Meeting the electrochemical society, Inc., 2004, Abstract No. 231, vol. 57, 235.

Shahverdi et al. "Rapid synthesis of silver nanoparticles using culture supernatants of enterobacteria: A novel biological apptoach", Process Biochemistry, May 2007, 42(5), 919-923.

Silver "Bacterial silver resistance:molecular biology and uses and misuses of silver compounds", FEMS Microbiology Reviews, Jun. 2003, 27, 341-353.

U.S. Appl. No. 12/307,190: Final Rejection, dated Jul. 17, 2012, 7 pages.

Lin et al., "A Further Insight Into the Mechanism of Ag+ Biosorption by *Lactobacillus* sp. Strain A09", Spectrochimica Acta Part A, Apr. 6, 2005, 6(61), 1195-1200.

Chinese Patent Application No. 200780025198.7: Chinese Fourth Office Action dated Mar. 20, 2012, 8 pages. (Redacted).

Fu, et al, "Spectroscopic Characterization on the Biosorption and Bioreduction of Ag (I) by *Lactobacillus* sp. A09," Acta Physico-Chimica Sinica, Sep. 2000, 16(9), 770-782.

Fu, et al., "Characterization of Adsorption and Reduction of Noble Metal Ions by Bacteria," Chemical Journal of Chinese Universities, 1999, 20(9), 1452-1454.

Zhang, et al, "Biosorption and Bioreduction of Diamine Silver Complex by *Corynebacterium*," Journal of Chemical Technology and Biotechnology, 2005, 80, 285-290.

* cited by examiner

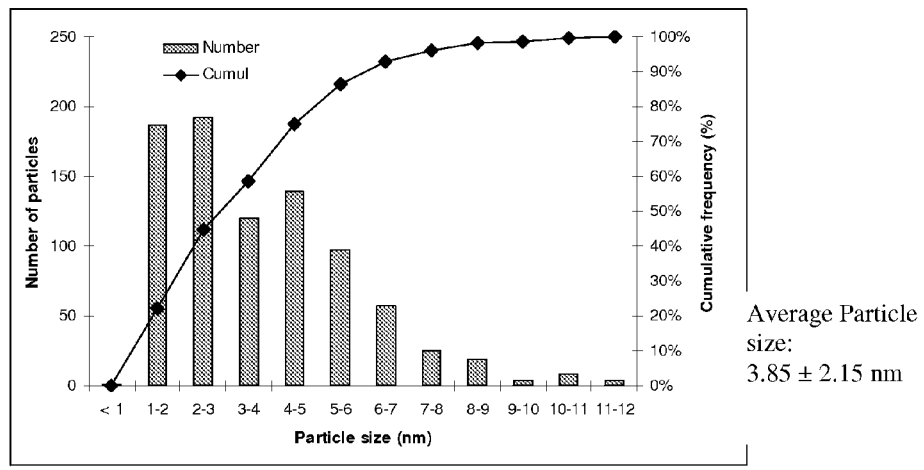
Average Particle size:
3.85 ± 2.15 nm
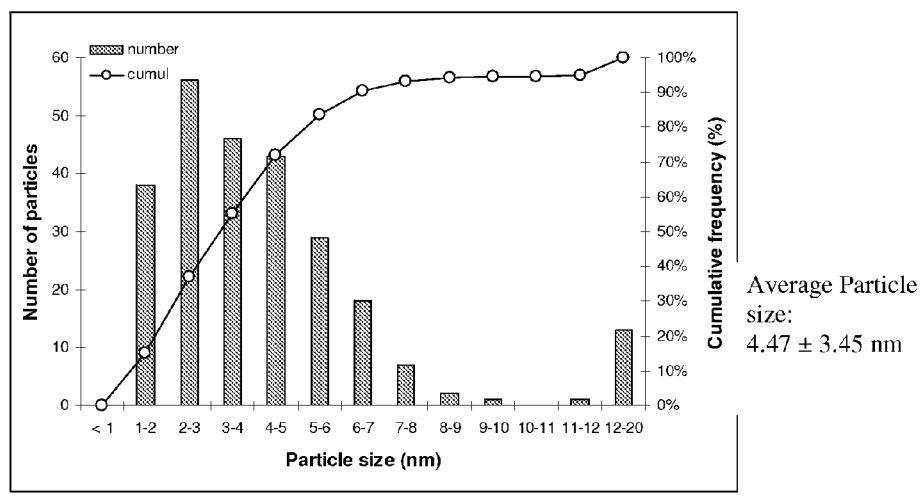
Average Particle size:
4.47 ± 3.45 nm

SILVER NANOPARTICLES WITH SPECIFIC SURFACE AREA AND A METHOD FOR PRODUCING THEM

CROSS-REFERENCE TO RELATED APPLICATIONS

This application is the National Stage of International Application No. PCT/EP2009/050019 filed Jan. 2, 2009, which claims the benefit of Great Britain Application No. 0800081.2, filed Jan. 4, 2008, the disclosures of which are incorporated herein by reference in their entireties.

The present invention relates to silver nanoparticles exhibiting specific physical properties, especially specific surface area characteristics and/or isoelectric point. The present invention relates to a novel method for producing silver nanoparticles, as well as anti-microbial compositions comprising such specific silver nanoparticles.

BACKGROUND OF THE INVENTION

Silver nanoparticles have valuable applications in the rapidly emerging field of nanomaterials. Exemplary silver nanoparticle applications include formulated biocides, antimicrobials and disinfectants, electronic chemicals, silver conductive ink, medical applications, wound care, solar panels and smart glass.

Although nanoparticles of silver in low concentration in aqueous and organic solutions are easy to prepare in a (physico-)chemical or photochemical way, their scaling-up needs a careful control of experimental conditions in order to avoid disparity from batch-to-batch. An increase in molar concentrations of the reagents generally results in an increase in particle size and agglomeration among particles. Since the benefit of nanoparticles is in their particle size, these are unwanted characteristics.

A typical chemical production process requires a dilute solution of silver salt, a surfactant or capping agent and a reducing agent. The solvent wherein the nanoparticles are produced can be water or an organic solvent such as N,N'-dimethylformamide (DMF). Most syntheses describe the use of suitable surface capping agents in addition to the reducing agents for synthesis of nanoparticles. Frequent use of organic compounds as well as polymers has been described for obtaining re-dispersible nanoparticle powders. These powders are normally post-treated by physical tempering, or alternative techniques such as thermal plasma processing, in order to obtain even smaller particles. The surface areas obtained from such methods is typically within a range not exceeding about 20 m$^2$/g, with particle sizes of about 30 nm.

Although nanoparticles of silver in low concentrations in aqueous and organic solutions are thus easy to prepare, scale-up remains difficult in order to control the size and prevent agglomeration of silver nanoparticles. Moreover, in view of the important fields of use of silver nanoparticles in formulated biocides, antimicrobials and disinfectants, the antimicrobial efficacy of the silver nanoparticles is crucial and is closely related to the physicochemical properties of the nanoparticles.

Since nanoparticles produced in this way are generally very expensive, applications in polymers have focused on generating silver nanoparticles in situ. The in situ synthesis of silver nano-particles in polymers as host materials is well established. When nanoparticles are embedded or encapsulated in polymer, the polymer acts as surface capping agent. Polymers such as poly(vinylalcohol), poly(vinylpyrolidone), polystyrene and polymethacrylate are all suitable polymers described in literature.

However obtaining zero-valent silver of desired shape, reactivity, and size distribution within the polymer matrix remains highly challenging. Moreover, important challenges remain in this approach, such as the stability of silver nanoparticles in the polymer, as well as the prevention of aggregate formation and minimal oxidation of the polymer. Thus there is still a need in the art for improving specific physical properties, especially specific surface area characteristics and/or isoelectric point, of silver nanoparticles, as well as for improving methods for producing silver nanoparticles.

SUMMARY OF THE INVENTION

In a first aspect, this invention relates to silver nanoparticles wherein the ratio of the average particle size to the specific surface area (BET) is from 0.015 to 0.15 nm/m$^2$/g and/or silver nanoparticles having an isoelectric point from 3 to 7. In another aspect, this invention relates to silver nanoparticles making out at least 20% by weight of a biocomponent from bacterial origin, said biocomponent containing at least 0.3% sulfur (S) by weight.

Silver nanoparticles according to any of the above specifications may be associated with 20 to 80% by weight, e.g. 30 to 70% by weight or 40 to 60% by weight, of a biocomponent of the genus *Lactobacillus*. Within said embodiment, the weight proportion of said biocomponent may be determined by any quantitative means such as, but not limited to, quantitative energy dispersive X-ray analysis. Within this embodiment, the silver nanoparticles may be distributed on or inside the cell envelope or S-layer or glycocalyx of the biocomponent.

Silver nanoparticles according to any of the above embodiments of the invention preferably have an average particle size from 1 to 8 nm, e.g. from 2 to 6 nm. Silver nanoparticles according to any of the above embodiments of the invention preferably exhibit a specific surface area (BET) from 30 to 90 m$^2$/g, e.g. from 35 to 85 m$^2$/g or from 40 to 80 m$^2$/g.

In a second aspect, this invention relates to method for producing silver nanoparticles, comprising the steps of:
 (a) incubating bacteria of the genus *Lactobacillus* with an aqueous solution comprising at least 4 mM of a silver salt in the presence of ammonia and an alkali metal hydroxide until a biomass of bacteria containing Ag$^0$ silver nanoparticles is formed, and optionally
 (b) extracting said Ag$^0$ silver nanoparticles from said biomass by means of concentrated alkali metal hydroxide or concentrated inorganic acid or enzymes.

In a preferred embodiment of this method, the bacteria used for the incubation step (a) are pre-treated for increasing the sugar-rich structures in their cell envelope, e.g. (but not limited to) by fermentation under a Carbon/Nitrogen ("C/N") ratio of at least 10:1, e.g. by fermentation in the presence of a fermentable sugar at a concentration of at least 20 g/L, preferably more than 50 g/L.)

In a preferred embodiment of this method, the bacteria used for the incubation step (a) are pre-treated by fermentation until their dry weight is increased by at least about 200%, e.g. by at least 300%, e.g. by fermentation during at least about 10 hours (e.g. during at least 15 hours or during at least 20 hours) and/or at a temperature within a range from about 4° C. to about 40° C.

In another preferred embodiment of this method, the bacteria used for the incubation step (a) are pre-treated by acidic hydrolysis of glycocalyx, cell envelope and/or S-layer, e.g. by acidic hydrolysis at a temperature above about 35° C.

In another embodiment of this method, the bacteria used for the incubation step (a) may be probiotic bacteria. Further details of alternative or preferred embodiments of this method are provided in the appended set of claims.

BRIEF DESCRIPTION OF THE DRAWINGS

FIG. 1: Particle size distribution of bionanosilver extracted from *Lactobacillus fermentum* obtained from several TEM microcopy analyses.

DETAILED DESCRIPTION OF THE INVENTION

In contrast to the known products, the silver nanoparticles of the present invention or produced by the present process unexpectedly have an increased antimicrobial reactivity, good dispersive behavior and a limited size distribution, and can be produced in high concentrations without the need for stabilizing polymers or potentially harmful organic molecules. This allows for a cost-effective production method, in which even the waste stream has added value.

In the present invention, a production process for silver nanoparticles is given, wherein the main component is a preferably post-treated biocomponent (e.g. a *Lactobacillus fermentum* strain G2/10), grown under specific conditions of a high C/N ratio. The silver nanoparticles of the present invention are not distributed randomly over the bacterial cell volume, but can be found in specific parts of the cell with different yet well-defined particle size ranges. With the current invention, well-defined particle size ranges can be obtained from the outmost cell fractions, hereafter referred to as either "glycocalyx" or "S-layer" or "cell envelope", for example with an average particle size of about 3-4 nm, whereas in prior art methods, broad particle ranges were obtained, for example 15 nm-500 nm for silver nanoparticles produced by *Lactobacillus* strains. Also, with the current method, easily 180 grams of colloidal silver can be produced per kilogram (dry weight) of biocomponent, whereas in other biological processes this process yield is much lower: e.g. 18 grams per kilo. By cell envelope it is meant the sum of cell wall, cell membrane and outer membrane, if present. The present method was found to be applicable to produce silver nanoparticles from a number of *Lactobacillus* species, including but not limited to *L. fermentum, L. brevis, L. casei, L. sakei, L. farciminis* and *L. parabuchneri* strains.

Importantly, the probiotic *Lactobacillus fermentum* G2/10 used in the following illustrative embodiment can be efficiently produced in fermentation devices at concentrations of about 10 kilograms (dry weight) of biocomponent per m³.

The growth of the biocomponent under a C/N ratio higher than 10:1 with a final C-source concentration of at least 20 g/L fermentable sugars, and preferably more than 50 g/L, e.g. 80 g/L glucose, combined with an optional hydrolysis step at low pH, and post-treatment of this biocomponent after cultivation with low concentrations of NaOH results in the production of small $Ag^0$ nanoparticles with a controllable size distribution in the bacterial glycocalyx, or &layer, or cell envelope. Both the reducing agent for Ag(I) reduction and the stabilizing agent for the produced nanoparticles, are inside of the saponified reaction mix. No addition of other reducing agents such as glucose is necessary during the $Ag^+$ reduction.

The bacterial cell wall of Gram positive *Lactobacillus* sp. is known to contain a thick layer of peptidoglycan, covered with lipoteochoic acids, teichoic acids, proteins and polysaccharides, followed by the more intracellular periplasmic phospholipids-containing membrane and then the cytoplasm. Peptidoglycan is N-acetylglucosamine β(1→4) N-acetylmaramic acid, and this oligosaccharide is the building block of long chains of heteropolysaccharides structuring the cell wall. There is also the extracellular glycocalyx, a viscous polysaccharide or polypeptide slime. The S-layer or surface layer is defined as the outermost part of the cell wall, composed of crystalline arrays of proteinaceous subunits.

In the current invention, producing silver nanoparticles with a uniform shape and a size in the range of 1-8 nm inside of the cell envelope, S-layer or glycocalyx with high efficiency is described. Three important aspects of the method are present:

1. The sugar-rich structures in the cell envelope are increased in number, and a thicker cell envelope of the biocomponent is obtained. This can be achieved by fermentation under a high C/N ratio of at least 10:1, for example by cultivating in a rich medium supplemented with a final glucose concentration of 80 g/L. This can be achieved by either gradual or stepwise increase of the C/N ratio during the fermentation process.

2. A way of further increasing the relative number of reducing sugars is by treating the dilute biocomponent in water with low concentrations of HCl while heating, e.g. 0.1 N HCl at 60° C., since this results in acid hydrolysis of the glycosidic bond in polysaccharides and oligosaccharides of the glycocalyx or peptidoglycan, thus generating more reducing sugars with free aldehyde or ketone groups under alkaline conditions. Optionally, this step may also be included during the fermentation, by including a step of exposure to low pH regimes. The amount of reducing sugars may be measured by using the Benedict's Reagent, containing Cu(II)O.

3. In a final step, the cultured biocomponent was washed with water and post-treated with 0.01-0.03 N NaOH. By reaction with NaOH or another base, hence in an alkaline environment, the anomeric $C_1$ atoms of the reducing monosaccharides in the bacterial cell wall structure become free for oxidation by $Ag^+$, due to restructuring around the anomeric $C_1$. Reducing sugars are sugars that are oxidized by $Ag^+$ under alkaline conditions. The reaction taking place is that of a free anomeric $C_1$ aldehyde or ketone group being oxidized to a carboxyl group. An example of a redox reaction of an anomeric $C_1$ aldehyde of a reducing sugar under alkaline conditions with $Ag^+$ is as follows:

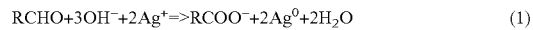

$$RCHO + 3OH^- + 2Ag^+ \Rightarrow RCOO^- + 2Ag^0 + 2H_2O \quad (1)$$

Surprisingly it is shown in this invention that by introducing $AgNO_3$, solubilized in $NH_3$, into a biocomponent produced and post-treated as described above, nanoparticle depositions of 0.9-7 nm $Ag^0$ are homogeneously dispersed over the glycocalyx, cell envelope and/or S-layer. The sum of glycocalyx, cell envelope and S-layer will be termed Outer Cell Compartments (OCC) for ease of reference. The bionanoparticles are stable in the OCC for at least 3 months and are furthermore extractable by differential extraction. Production of such homogeneous $Ag^0$ by this method is enhanced by NaOH, since the oxidation of $Ag^+$ by reducing sugars is improved under alkaline conditions to generate oxidizable anomeric aldehyde or ketone groups. Ketoses can also be reducing sugars when isomerised to aldoses via an enediol, as shown in the following reaction:

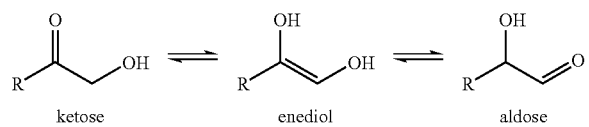

ketose ⇌ enediol ⇌ aldose

More anomeric $C_1$ carbon positions become available for reduction of $Ag^+$ in the presence of NaOH, other metal hydroxides or bases, due to restructuring around the anomeric $C_1$ leading to a ring-opening of the cyclic aldose or ketose. Hence, the number of formation sites and nucleation sites for $Ag^0$ is much higher, resulting in more $Ag^0$ particles deposited in a more homogeneous way, when compared to the production of $Ag^0$ in the same *Lactobacillus* without post-treatment with NaOH. This can also be observed by comparing Electron Microscopy analyses. With the method here described, small nanosilver deposits inside of the outer cell envelope can clearly be differentiated from the larger $Ag^0$ crystals inside the cytoplasm. Without NaOH, prior art methods clearly result in the absence of deposition of small nanometric silver particles inside of the cell envelope or glycocalyx. Also, with NaOH, the phospholipid bilayers are saponified, resulting in more permeable cell membranes.

The solubilization of $AgNO_3$ in $NH_3$ prevents immediate precipitation of $Ag_2O$ or $Ag(OH)$ in an alkaline environment. $NH_3$ complexes the $Ag^+$, thus keeping it better in solution and allowing a better interaction with the biocomponent.

Silver nanoparticles produced according to the invention can be further separated from the biocomponent. In a first step, the smallest bionanoparticles are extracted from the OCC and this fraction typically contains at least 55% of silver particles smaller than 4 nm, at least 15-20% of silver particles smaller than 2 nm, and this results in a population with an average particle size of about 1-8 nm. After this first extraction step of the OCC, the intracellular portion of nanoparticles with larger particle sizes (>20 nm-200 nm) remains with residual fractions of the biocomponent in a residual waste stream, which can be turned into a product with added value.

According to this invention, desired size ranges can be extracted out of different locations of the saponified biocomponent: small silver nanoparticles with an average size around 3-4 nm may be produced in high concentrations in the glycocalyx, cell envelope and/or S-layer, which can be differentially extracted from the larger silver nanoparticles (20-200 nm) located in other parts of the bacterial cell, for instance in the cytoplasmic region. The pre-treated biocomponent, e.g. *Lactobacillus fermentum*, has a thick glycocalyx and/or cell envelope, rich in reducing sugars.

In the present invention, it was found that by post-treating a *Lactobacillus fermentum* suspension in water with 0.01-0.03 N NaOH during 15 minutes, a saponified biocomponent is obtained with high reducing power for the reduction of Ag(I) to metallic Ag(0) within several hours (e.g. 0.5-16 hours) and with a Ag(I) to Ag(0) conversion efficiency of more than 80% (e.g. 95%). The resulting $Ag^0$ nanoparticles deposited in the glycocalyx of the saponified biocomponent were found to be stabilized by a biogenic coating rich in C and O and containing biogenic S and N, by means of Energy Dispersive X-ray Diffraction (EDX) and (FT)IR spectrometry. S-containing ligands such as thiol, present in amino acid residues such as cysteine and methionine, may also contribute to $Ag^0$ formation by the following mechanism.

A representative example of a redox reaction of a sulfhydryl containing biocomponent with $Ag^+$ is as follows:

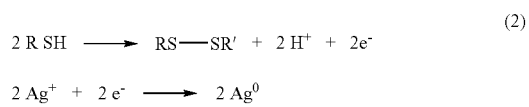

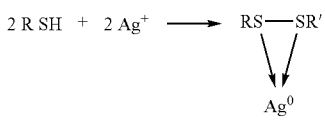

or alternatively:

$$RSH + Ag^+ \rightarrow RS\text{—}Ag + H^+ \quad (3)$$

Since the molar ratio of S to Ag in the bionanosilver on biocomponent is between 1:4 to 1:60, only a part of the biogenic $Ag^0$ can be attributed to the precipitation of $Ag^+$ by sulfhydryl as in reaction (2), and a part of the $Ag^0$ was produced by reaction (1). The positive effect of NaOH on $Ag^0$ precipitation efficacy can for instance be related to the solubilization of proteins or the reaction with reducing sugars.

The elemental silver $Ag^0$ that is thus produced can be bound to biogenic disulfide by means of a dative covalent bond, sharing the free electron pair of the S, or alternatively, the silver ion interacts with a sulfhydryl group, and forms a —SAg linkage (3). In this way, the nanosilver particles produced with the method here described, always contains some amount of biogenic sulfur that is bound to the $Ag^0$ particle, and stabilizes the $Ag^0$ dispersion by ligand-formation.

Interestingly, surface (S-) layers of protein or glycoprotein subunits, called S-layers in bacteria, can physically mask the negatively charged peptidoglycan sheet and thus prevent auto-agglutination, as was demonstrated e.g. in *Bacillus stearothermophilus*. In contrast to most bacterial species, the S-layer proteins in *lactobacilli* are highly basic, with an iso-electric point above pH=9. Hence, the role of the S-containing functional groups that are bound to the $Ag^0$ nanoparticles produced by this method, may be to prevent agglomeration by masking the negative charge of the biogenic surface layer originating from the cell envelope or glycocalyx, on the $Ag^0$ particles. This would result in an iso-electrical point (IEP) that is more in the higher pH region, as was demonstrated by zeta potential measurements: less protons are needed to make the zeta potential from the nanosilver produced with the method here described switch from negative to positive when compared to nanosilver prepared in other ways. The IEP of the bionanosilver was found to be around pH 4-5 which is higher than the IEP from *Lactobacillus* strains containing a significant S-layer. This may indicate an enrichment in S-layer type proteins on the nanosilver surface, which agrees well with the biogenic S and N content present on the nanoparticles, as detected by quantitative EDX (Table 4). This represent a valuable asset, since this organic layer may endow dispersive behavior to the nanoparticles, as was observed by TEM microscopy (not shown). Organic ligands improve the utility of nanoparticles by preventing their aggregation and agglomeration. These ligands can also endow nanoparticles with important recognition, transportation and catalytic properties.

By a post-saponification step, the intracellular cytoplasmic region as well as the glycocalyx, cell envelope and/or S-layer were found to become a site of Ag(0) production and accumulation. Contrary to what is mentioned in literature, the sizes of the silver nanoparticles produced in the OCC are in the range of 0.9-7 nm, whereas larger nanoparticles in the range of 20-200 nm are not found in the OCC but rather in the cytoplasm. The nanoparticles from the OCC can be selectively extracted, e.g. by an acid extraction, which results in a nanosilver product with an average particle diameter of 3-4 nm. The larger particles, i.e. those larger than 7 nm constitute at most a few percent of this OCC extract. The nanoparticles in our invention do not agglomerate or form clusters inside the glycocalyx, even after 2 months of storage at 4° C. The post-saponification thus allows for a diffusion of Ag(I) or Ag(0) into the OCC and cytoplasmic regions, and the post-saponified cell constituents rich in C and S stabilize crystal growth and are likely to protect the individual nanoparticles by a charged organic layer of biological origin. $AgNO_3$ is preferentially used as the silver salt for nanosilver production by this method. By the present method, scale-up to 1 $m^3$ batches was found to be feasible, and allowed for a cost-effective production process, where at least 6 mM, and preferably 10 mM of $AgNO_3$ was effectively converted to Ag(0) nanoparticles with the properties disclosed elsewhere in this document. The presence of $NH_4^+$ allowed for the formation of a $Ag(NH_2)^+$ or $[Ag(NH_3)_2]^+$ silver(I)-ammonia complex that on the one hand allowed for better electrostatic interactions between Ag(I) and the reducing groups in the OCC, and on the other hand prevented the formation of Ag(I)O or Ag(I)OH in the presence of NaOH in the reaction mix. The addition of ammonia to the reaction mix could be limited to 0.25 kg $NH_3/m^3$ without formation of Ag(I)O, Ag(I)OH or silver oxides in general.

Reaction of ammoniacal silver with cationic amino acids like arginine and histidine can result in increasing $Ag^0$ precipitation. Such alkaline amino acids can for instance be a substantial part of the glycocalyx, cell envelope or S-layer. These amino acids may play a role in coordinating the Ag(I) so that is can further be reduced to Ag(0) by surrounding reducing sugars.

In the current context, the nanosilver particles thus produced were tested as an effective antimicrobial and biocide. Recent commercial developments, for instance by Hygate, have shown that nanosilver embedded in a porous matrix allows for a slower, more controlled release of antimicrobial $Ag^+$ than when ionic silver is embedded in an inert, porous matrix. Also in polymer and plastic formulations, silver nanoparticles would have certain benefits. The large specific surface area of silver nanoparticles produced by the method here described, allows for a more effective antimicrobial action, better dispersive behavior in water or other solvents and good interaction with matrices like zeolites for embedding the nanoparticles. Antimicrobial nanosilver particles can be effectively used for surface coatings, for example in medical applications and in water treatment filters.

One advantage of formulating the bionanoparticles described in this invention into polymers, for example in an aqueous dispersion of an acrylic ester copolymer, is the good dispersive behavior of the bionanoparticles in the polymer, thus preventing agglomeration, which is related to the surface potential and biogenic surfactant molecules at the particle surface which are due to the methods described here. The surface potential relates to the iso-electric point of the particle surface, which is at a significantly higher pH of >4-5, than with nanoparticles produced in other methods, as shown by zeta potential measurements.

The good dispersion in water of nanoparticles with an average size of 3-4 nm has obvious advantages for formulation into water-based paints or polymers. As a result of good dispersion, little agglomeration is observed and the total surface area of the silver particles inside the polymer is larger, thus leading to higher antimicrobial reactivity. An example of such an aqueous based polymer is the acrylic ester based Rhodopas Ultrafine PR3500 (Rhodia, France). Such an acrylic ester polymer can be represented by the structural formula of $(-CH_2CHCOO-)_n$.

The same advantage of increased antimicrobial activity coupled to good specific surface area and particle stability due to little agglomeration and a positive surface potential in a broader pH range, leads to better interaction with porous zeolites. An example of such zeolite is the Zeolith N (Zeolite Aluminium silicate, Evers E. K., Hopsten, Germany) where it was shown that the bionanoparticles are well retained in the zeolite matrix and result in a higher antimicrobial reactivity than $Ag^+$-zeolite combinations, even when water with high salinity is passed over the surface of the zeolite. Other natural microporous minerals like celite are also suitable for combination with the bionanoparticles produced by this invention. The zeta potential of the nanosilver thus produced, being negative at a pH higher than 4, allows good retention of the nanosilver in ion exchange resins at high and neutral pH. Ion exchange resins may thus be suitable for combining with bionanosilver for the co-ordinated release of $Ag^+$ at differential pH.

Both fractions of nanoparticles, either extracted from the glycocalyx/cell envelope or from other parts of the bacterial cell, may be combined when this is advantageous in certain applications.

Some advantages of the present invention are as follows:

[1] Many silver-based biocides used for formulation into polymers, paints, textile fibers or sealants, utilize ion exchange resins or compounds to bind and exchange $Ag^+$. A typical commercial compound used for $Ag^+$ exchange is zeolite. Moreover, such $Ag^+$ exchange systems are very sensitive to $Ag^+$ depletion, for instance when water with high cationic strength passes over them. This significantly lowers the durability of such systems. On the other hand, most of the microorganisms which are contemplated for use in this invention are cheaply and easily produced in large quantities. For example, most common *Lactobacillus* bacteria can be produced in large quantities. The bionanoparticles prepared by the method described here can not only be produced within a narrow size range, for example around 3-4 nm on average, but can furthermore be used as a source of controlled $Ag^+$ release, retaining high antimicrobial activity over time, both inside polymers, inside porous resins or other compounds, and in dispersions.

[2] A large number of microorganisms have a polysaccharide-rich glycocalyx or S-layer which contains proteins. With the discovery of the effect of saponification on differential nanoparticle production and size distribution inside bacterial glycocalyx and other cell constituents, it is now possible to provide a simple and effective method of producing very small silver nanoparticles by post-saponifying microbiotic biomass produced by fermentative or other processes, and differentially extracting from this biomass afterwards.

[3] Methods of the invention also offer a substantially improved conversion of silver salt into silver nanoparticles. Conversion to nanoparticles of 95% of the silver contained in the silver salt, for example, may be achieved within 16 hours at 20° C. at concentrations of 1000 mg $Ag^+$ and 4600 mg *Lactobacillus* biomass (dry weight) in the final reaction mix. Depending on the reaction conditions (including concentrations of reactants, temperature, stirring and the like), conversions of more than 80% may be achieved within 30 minutes.

[4] the size distribution of the resultant silver nanoparticles is relatively tight and can be at least partially tuned by differential extraction. For instance, the sizes of the extracted silver nanoparticles produced in the glycocalyx usually are in the range of 0.9-7 nm. In general, small nanoparticles with good dispersive behavior result in very limited agglomeration. The smaller the nanoparticles, the less silver is generally needed to obtain antimicrobial properties.

[5] The bionanoparticles thus produced and extracted contain still measurable amounts of biogenic S, N, C and O. This organic layer associated with the produced nanoparticles results in a surface potential and dispersive behavior of the nanoparticles. Furthermore, this organic layer may have a bridging effect towards biological structures. The combination of these effects increases the antimicrobial effectiveness of the silver nanoparticles.

[6] The fraction of larger silver nanoparticles (20-200 nm) that is extracted from cell constituents other than the glycocalyx, still was found to have good antimicrobial effectiveness. Moreover, these particles are in a size range suitable for electronic chemical applications, where flexible conductive circuit lines are typically at least twice as thick as the constituting conductive nanoparticles. For instance a line of 120 nm can be printed with a conductive ink containing 60 nm silver nanoparticles. Interestingly, it was found that silver parts printed using nanosilver suspensions are significantly enhanced in sintering quality, especially when silver parts have thin or small features with high aspect ratios. In the present invention, the larger bionanosilver particles extracted from the biocomponent have an irregular shape, with silver protrusions possibly resulting from fusion with smaller nanoparticles.

These irregularities may assist in (i) a larger specific surface area of the larger particles, contributing to relatively good MIC efficiencies (see Table 7a), and (ii) better selective joining with microsilver powder in rapid manufacturing or prototyping.

[7] The stabilization of the bionanosilver particles can occur with the weak functional groups present in the saponified biomass, e.g. (i) by aminocarboxylates (e.g. amino acids), (ii) hydroxyl groups present in the saponified biomass, or (iii) donor ligands such as thiols and/or amines. Amines and/or thiol-bearing molecules were found conjugated to silver nanoparticles according to this method, allowing long-term storage (weeks or months) of silver nanoparticles without appreciable agglomeration.

[8] Since the bionanosilver particles show a high UV absorption maximum at 425 nm, even at low concentrations of 40 mg/L Ag, UV spectrometry is a straightforward quality control parameter.

[9] The bionanosilver particles show excellent biocidal properties against algae, Gram positive bacteria, Gram negative bacteria, Fungi (molds and yeasts). Since the smallest particles are about 1 nm, and approximately 10% of the nanoparticles are of this size, good viricidal properties may be achieved against HIV-I and other viri.

[10] Controlled, pH-based release of Ag from ion exchange resins, compared to other silver nanoparticles.

The present invention may be better understood by reference to the following examples, which are for purposes of illustration, and are not intended to limit the scope of the invention:

1. Production of Bio-$Ag^0$ Nanoparticles Using a Post-Saponified *Lactobacillus* Biocomponent.

The *Lactobacillus* G2/10 strain was cultured in MRS broth
Two batches of pre-culture were prepared in 2 times 1500 ml MRS broth in erlenmeyers and shaken at 100 rpm (30° C.)
A feed fermentor was prepared with a total volume of 100 L, containing 24 kg glucose in 40 L water (0.6 kg/L)
Optical Density (DO) analyses were used to determine the dry matter in the culture broth, a calibration was made in a culture flask containing G2/10 in MRS broth
The glucose concentration was followed and HPLC vials were prepared for analysis of lactate MRS broth (without sodium acetate) was prepared as follows. For 1 L, the following additives were used:
In 900 ml water the following products from Organotechnie (La Courneuve, France) were dissolved:

| | |
|---|---|
| Casein peptone N1: | 10 g |
| Yeast Extract M1: | 5 g |
| $K_2HPO_4$: | 2 g |
| $MgSO_4 \cdot 7H_2O$: | 0.1 g |
| $(NH_4)_2$citrate: | 2 g |
| $MnSO_4$: | 0.05 g |
| Tween 80: | 1 g (1 ml) |

This solution was sterilized in an autoclave reactor. In 100 ml water, 20 g glucose was added. This solution was sterilized by filtration.

The 900 ml and 100 ml solutions thus prepared were added together after sterilization, and the pH was adjusted to 6.

To make solid medium, 15 g of agar was added to one liter of MRS broth, and in some cases bromocresol purple as an indicator.

A fermentor of 400 L was inoculated with 1 pre-culture batch of 1500 ml. The glucose additions were realized by pumping the glucose solution of 0.6 kg/L from the feed fermentor to the 400 L culture fermentor. To the culture fermentor, 260 L MRS broth was added, and the broth was sterilized. Then, 10 L glucose feed solution was pumped into the culture fermentor, the *Lactobacillus fermentum* G2/10 was added to the culture broth, and the fermentation process was started to grow the bacterial culture. The culture of the bacil is explained in detail below. Further details on the fermentation are given in Tables 1a and 1b.

TABLE 1a

Engineering parameters during *Lactobacillus fermentum* G2/10 fermentation: oxygen transfer coefficient Kla related to oxygen transfer rate (vvm) and agitation speed (peripheric speed in m/s and rotational speed in rpm)

| | SF 20L | US 400L | | |
|---|---|---|---|---|
| Parameters | 100 rpm 0.1 VVM | 100 rpm 0.1 VVM | 100 rpm 0.05 VVM | 50 rpm 0.1 VVM |
| Peripheric Agitation Speed (m/s) $\pi$ND | 0.524 | 1.325 | 1.325 | 0.662 |
| Kla ($h^{-1}$) $0.026(P_{actual}/V_{liq})^{0.4} \cdot ((G/V_{liq}) \cdot H_{liq})^{0.5} \cdot 3600$ | 8.4 | 24.4 | 18.5 | 10.2 |

$G (m^3/s) = VVM * V_{liq}/60$
$P_{actual} = 0.34 Np^{0.5} (P^2 \cdot N/60 \cdot d^3/G^{0.56})^{0.45}$ with $P = Np \cdot \rho(N/60)^3 \cdot d^5 \cdot$ Nb turbine TABLE 1b Glucose substrate concentration, lactate metabolite concentration and *Lactobacillus* dry weight during fermentation of *L. fermentum* G2/10 in a 400 L fermentor.

| Time (hours) | Biocomponent Dry Weight (g/l) | Glucose (g/l) | Lactate (g/l) |
|---|---|---|---|
| 0.0 | 0 | 20 | 0 |
| 3.0 | 0.01 | 18 | 0.5 |
| 4.5 | 0.2 | n.a. | 1.75 |
| 10.0 | n.a. | 12 | n.a. |
| 23.0 | 1.2 | 1.5 | 13 |

TABLE 1b-continued

Glucose substrate concentration, lactate metabolite concentration and *Lactobacillus* dry weight during fermentation of *L. fermentum* G2/10 in a 400 L fermentor.

| Time (hours) | Biocomponent Dry Weight (g/l) | Glucose (g/l) | Lactate (g/l) |
|---|---|---|---|
| 24.0 | 1.2 | 2 | 13 |
| 25.0 | n.a. | 50 | n.a. |
| 26.5 | 3 | n.a. | n.a. |
| 27.5 | 7.5 | 30 | 30 | n.a. = not available

The fermentation parameters were:
Temperature: 30° C.
Agitation: 50 rpm
pH set point: 6
Aeration: set point 0.1 VVM (air volume/liquid volume per minute); partial $PO_2$ pressure was not regulated
Initial glucose concentration: 20 g/L Other fermentable sugars that are suitable for growth of bacilli, are for example sucrose, maltose and fructose, which may be added directly or as part of a polysaccharide (e.g. starch) or extract (e.g. corn sugar, rice sugar, molasses, milk whey) to the growth medium.

The monitoring of physicochemical parameters during *Lactobacillus* G2/10 fermentation indicates a drop in $pO_2$ from 6 hours culture onwards, continuing until 12 hours. The $pO_2$ then ascends to a value of 65-70% during 3-4 hours, before dropping again. This temporary ascent is due to a postponed 5 L glucose dosage after 14 hours. It is preferable to dose this glucose between 11 and 12 hours culture. The second automated glucose injection of 5 L (0.6 kg/L) took place after 20 hours, when the $pO_2$ was minimal. A third glucose injection of 20 L was done between 23 and 24 hours of culture, when it was observed that glucose had been exhausted. Only after this third injection did the *Lactobacillus* start growing significantly. In fact, the biomass increased from 1 g/L to 7 g/L in less than 3 hours. At this moment, the final bacterial density had reached 4,6 $E^9$ CFU/ml (Colony Forming Units). The generation time was thus 1.5 hour between 0 and 6.5 hours of culture (lag phase) and 2.7 between 24 and 27.5 hours of culture (exponential phase).

The biocomponent was harvested in exponential phase after 27.5 hours of culture, when the *Lactobacillus* was in full growth activity and the residual glucose concentration was 30 g/L. This information suggests that further increase of the biocomponent dry matter is likely when the fermentation process is further optimized to avoid intermediate increase of the $pO_2$ and maintain a (hetero-)fermentative environment. From the remaining glucose in the medium after 27.5 hours, it is clear that not all glucose was converted to biomass and that the biomass was not influenced by almost 50 g/L glucose in the medium. In fact, the second and third glucose dosages were far more effective than the first. This indicates that 15 kg of glucose has been consumed by 2.25 kg of biocomponent, thus indicating a substrate yield of $Y_x/S=0.15$.

The lactate concentration reached almost 30 g/L at the end of the fermentation, which gives a total of 8.7 kg of lactate for a conversion yield of $Y_p/S=0.57$. Lactate production follows the same trend as the biocomponent dry matter in the growth medium. There was a temporary drop in pH to about 4, due to sudden exponential lactic acid increase.

At the end of fermentation, the biocomponent was harvested by centrifugation (continuous centrifuge, Alpha-Laval, 500 L/h), resulting in a cream of 15 liters at 13.6% by weight biocomponent (dry matter). This cream was consequently washed twice with deionized water and re-centrifuged. During centrifugation and washing, biomass losses were observed and a final washed biocomponent slurry of 14 liters at 8% by weight biocomponent (dry matter) was obtained. This washing step and biocomponent harvest can be optimized by increasing centrifugation speed and combining with filtration (e.g. cross-flow filtration) in order to obtain more than 95% recovery of the biocomponent (dry matter) from the fermentation broth.

Hence, bionanosilver production was started with 1120 g (dry weight) washed biocomponent G2/10. This biocomponent was mixed with 250 liters of de-ionized water in a 1 $m^3$ plastic container (2×1×0.5 l×b×h). Soda (NaOH) was added from a 10 N NaOH stock solution to a final concentration of 0.03 N NaOH in the biocomponent in water suspension. The pH of this solution was 11.5. This reaction was mixed well during 15 minutes in order to obtain a saponification of the biocomponent. Next, 392.5 g of silver nitrate ($AgNO_3$) was solubilized in 417 grams of a 15% $NH_3$ solution in water. This solution was further mixed into the post-saponified biocomponent suspension and allowed to react at 20° C. during 16 hours under mild stirring.

From ICP-MS (Inductively Coupled Plasma-Mass Spectrometry) and XRD analyses on the dry matter and the supernatant after centrifugation, it was found that 98% of $Ag^+$ had been converted to $Ag^0$ after 16 hours. The mixture was consequently centrifuged (Alpha Laval continuous centrifuge, 500 L/h) and washed twice with deionized water to remove residual nitrate, soda and ammonia. A final product of 15.2 liters was obtained, containing a final $Ag^0$ concentration of 9302 mg/L. This final product contained only traces of nitrate and ammonia, amounting to at most 4 mg/L N, as determined by ion chromatography and TAN determination. Due to washing and centrifugation, approximately 44% of $Ag^0$ and biocomponent dry weight were lost. This resulted in a $Ag^0$ recovery of 56% compared to initial $Ag^+$ added to the reaction, although 98% conversion to $Ag^0$ had been determined in the reaction mixture. The losses were due to lack of high speed centrifugation, and hence washout of the product during centrifugation. In later small scale testing it was found that 10,000 g centrifugation or ultracentrifugation is a preferential technique to avoid $Ag^0$ nanoparticle loss during washing and harvesting. Also filtration will furthermore be tested.

2. Extraction of Bionanosilver

The goal of these tests was to set up a reaction with the biocomponent containing silver, in order to free silver nanoparticles from the bacterial structures. Three experiments were set up, wherein three different chemical reagents were brought into contact with a quantity of biocomponent containing nanosilver produced by the method described earlier, as follows: (i) hydrogen peroxide ($H_2O_2$, 35% by volume in water), (ii) NaOH (0.05-2 N) and (iii) $H_2SO_4$ (0.4-9.8 N).

$H_2O_2$ was added to a suspension of biocomponent containing silver in water, to a final concentration of 15% $H_2O_2$. The reaction was highly exothermic and heavy foam formation occurred. After 24 hours of reaction, the mixture was sonicated. Approximately 15% of silver weight was extracted from the biocomponent by this method. This 15% contained mostly the nanosilver particles between 1-7 nm originating from the glycocalyx, cell envelope and/or S-layer.

Similar results could be obtained by enzymatic hydrolysis, for example by using lysozym. A clear, brownish supernatant was observed shortly after addition of 4 g lysozym to 1 L water containing 1000 mg/L Ag in the form of nanosilver on biocomponent.

Results from NaOH and $H_2SO_4$ extractions are shown in Tables 2 and 3. Best results were obtained with $H_2SO_4$, where approximately 10% of silver weight was extracted from the biocomponent, even at 2 N $H_2SO_4$ and 0° C. after 10 minutes. The reaction was exothermic, but no foam formation occurred.

TABLE 2

Effect of different NaOH concentrations, temperatures and reaction times on the extraction efficacy of nanosilver from the biocomponent-silver matrix. The initial mass of Ag bound to the biocomponent as nanosilver was 52.4 mg.

| Temperature (° C.) | Concentration NaOH (N) | Incubation time (h) | Mass Ag removed from biocomponent (mg) | nanoAg-recovery yield by soda treatment (%) |
|---|---|---|---|---|
| 60 | 0.05 | 0.17 | 0.15 | 0.28 |
| 60 | 0.5 | 0.17 | 0.17 | 0.33 |
| 60 | 1 | 0.17 | 0.25 | 0.49 |
| 60 | 2 | 0.17 | 0.50 | 0.96 |
| 80 | 0.05 | 0.17 | 0.06 | 0.11 |
| 80 | 0.5 | 0.17 | 2022 | 4.23 |
| 80 | 1 | 0.17 | 2.74 | 5.23 |
| 80 | 2 | 0.17 | 2.43 | 4.64 |
| 100 | 0.05 | 0.17 | 0.16 | 0.31 |
| 100 | 0.5 | 0.17 | 3.05 | 5.81 |
| 100 | 1 | 0.17 | 3.06 | 5.84 |
| 100 | 2 | 0.17 | 2.83 | 5.40 |
| 100* | 0.05 | 0.08 | 0.28 | 0.54 |
| 100* | 0.5 | 0.08 | 0.26 | 0.49 |
| 100* | 1 | 0.08 | 0.09 | 0.17 |
| 100* | 2 | 0.08 | 0.28 | 0.53 |
| 100* | 0.05 | 0.17 | 0.13 | 0.25 |
| 100* | 0.5 | 0.17 | 0.07 | 0.14 |
| 100* | 1 | 0.17 | 0.20 | 0.38 |
| 100* | 2 | 0.17 | 0.26 | 0.50 |

TABLE 3

Effect of different $H_2SO_4$ concentrations and temperatures on the extraction efficacy of nanosilver from the biocomponent-silver matrix. The initial mass of Ag bound to the biocomponent as nanosilver was 262 mg. The reaction time was 10 minutes.

| Temperature (° C.) | Concentration $H_2SO_4$ (N) | Mass Ag removed from biocomponent (mg) | nanoAg-recovery yield by acid treatment (%) |
|---|---|---|---|
| 0 | 0.40 | 8.34 | 3.18 |
| 0 | 0.80 | 21.02 | 8.02 |
| 0 | 1.60 | 25.92 | 9.90 |
| 0 | 4.90 | 17.92 | 6.84 |
| 0 | 9.80 | 30.22 | 11.54 |
| 60 | 0.40 | 14.50 | 5.54 |
| 60 | 0.80 | 20.18 | 7.70 |
| 60 | 1.60 | 21.20 | 8.09 |
| 60 | 4.90 | 28.98 | 11.06 |
| 60 | 9.80 | 32.36 | 12.35 |
| 80 | 0.40 | 18.24 | 6.96 |
| 80 | 0.80 | 11.32 | 4.32 |
| 80 | 1.60 | 24.88 | 9.50 |
| 80 | 4.90 | 19.24 | 7.34 |
| 80 | 9.80 | 31.10 | 11.87 |
| 100* | 0.40 | 24.06 | 9.18 |
| 100* | 0.80 | 14.34 | 5.47 |
| 100* | 1.60 | 36.04 | 13.76 |
| 100* | 4.90 | 22.54 | 8.60 |
| 100* | 9.80 | 29.84 | 11.39 |

In the following example, a complete extraction of "biocomponent with nanosilver" with $H_2SO_4$ is given in detail, based on differential extraction and centrifuge steps, resulting in different fractions of nanosilver: first the fraction originating from the OCC and containing silver nanoparticles as small as 1 nm-7 nm. In consecutive extraction steps the fraction originating from the cell cytoplasm and other cell regions was extracted, containing nanoparticles on average larger than 20 nm.

The 150 mL water suspension of biocomponent with nanosilver obtained by this method contained 7300 mg Ag/L as determined by ICP-MS analysis. To this 150 mL, 50 mL $H_2SO_4$ (98%) was added.

The total volume amounted thus to 200 mL (25% $H_2SO_4$), containing 5480 mg Ag/L. This mixture was allowed to incubate at 20° C. during 16 hours.

The mixture was centrifuged at 11,800×g during 30 minutes and this resulted in the separation of two fractions: a supernatant$_1$ and a pellet$_1$.

Supernatant$_1$ was found to contain 3480 mg Ag/L.

The nanosilver in supernatant$_1$ was precipitated by neutralizing the 200 mL 25% $H_2SO_4$ suspension with 10 N NaOH by titration. The nanosilver was agglutinated and could therefore be harvested by gravitational sedimentation or centrifugation from the salt-rich brine. These flocs were washed twice with de-ionized water, and separated from the washing water by centrifugation at 11,800 g. After the washing steps, the nanosilver could be easily dispersed in water to form a stable colloidal suspension without visible agglomeration. The resulting "Extracted bionanosilver" was found to be associated with a significant amount of organic biogenic material (shown in Table 4 under 'Extracted bionanosilver'). The fraction of small silver nanoparticles containing a significant biogenic coating of organic material (detectable by IR spectrometry) could be separated from a fraction of nanoparticles containing less organic material (shown in Table 4 as Extracted bionanosilver after washing) by differential centrifugation at 3000 g for 5 minutes. The S-content of the material associated with the extracted bionanoparticles was the same when this extraction step was performed with phosphoric acid as compared to suphuric acid, after several washing steps with deionized water. This indicates that the S component originated from the biocomponent in the extracted fractions, probably as a part of proteinaceous material as determined by (FT)IR.

The nanosilver that was thus collected was found to have excellent dispersive qualities and had a size range between 0.9 and 7 nm (FIG. 1). The nanosilver in the final washed pellet did not result in a detectable amount of associated organic material by IR spectrometry, but by EDX there was still a detectable organic layer as shown in Table 4 (extracted bionanosilver after washing).

The extracted biocomponent harvested in pellet$_1$ was examined by electron microscopy. It was found that the OCC of the remaining *Lactobacillus fermentum* biomass were ruptured and the nanosilver was removed from inside the OCC.

TABLE 4

Quantitive Energy Dispersive X-ray analysis of bionanosilver produced by the present method, compared to nanosilver produced on *Lactobacillus fermentum* by the method from Lin et al. (2005)

| Element | Wt % |
|---|---|
| | Bionanosilver on biocomponent |
| C | 57.03 |
| N | 11.79 |
| O | 24.45 |
| Na | 1.14 |
| P | 0.8 |

TABLE 4-continued

Quantitive Energy Dispersive X-ray analysis of bionanosilver produced by the present method, compared to nanosilver produced on *Lactobacillus fermentum* by the method from Lin et al. (2005)

| Element | Wt % |
|---|---|
| S | 0.22 |
| Ag | 4.52 |
| Nanosilver produced on *Lactobacillus fermentum* by the method from the prior art | |
| C | 59.9 |
| N | 14.67 |
| O | 24.84 |
| Na | 0 |
| P | 0.25 |
| S | 0.06 |
| Ag | 0.23 |
| Extracted bionanosilver | |
| C | 57.33 |
| N | 7.98 |
| O | 10 |
| Na | 0.12 |
| P | 0.24 |
| S | 0.3 |
| Ag | 23.08 |
| Extracted bionanosilver (after washing) | |
| C | 16.47 |
| N | 0 |
| O | 4.37 |
| Na | 1.06 |
| P | 0 |
| S | 1.21 |
| Ag | 75.73 |
| Residual bionanosilver | |
| C | 22.83 |
| N | 0.85 |
| O | 16.26 |
| Na | 0.14 |
| P | 0.05 |
| S | 4.46 |
| Ag | 51.74 |

This remaining biocomponent was further extracted to remove the residual silver nanoparticles from the remaining bacterial structures (among others the cytoplasm).

50 mL $H_2SO_4$ (98%) was added to homogenize pellet$_1$ in a suspension containing 3016 mg/L Ag. This homogenate was allowed to react at 20° C. during 16 h. After centrifugation at 11,800×g for 30 minutes, there was a separation into a supernatant$_2$ and a pellet$_2$. The pellet$_2$ was investigated by Electron Microscopy. Silver nanoparticles between 20 and 200 nm in size were agglomerating between residual fractions of biomatrix. The organic association of these nanoparticles was confirmed by IR spectrometry. In terms of silver mass balance, the following scheme can be drawn for this experiment.

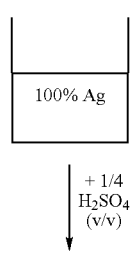

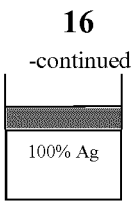

Approximately 60% of total Ag weight could be recovered by the first extraction step in 25% $H_2SO_4$, resulting in a mix of organic remnants and silver nanoparticles. Out of this stream, the silver nanoparticles could be further purified by differential extraction and washing steps with de-ionized water, as described earlier. The resulting silver nanoparticle suspension in water was characterized by EDX (Table 4), Electron Microscopy, Zeta Potential, UV spectrometry, XRD, Specific surface area measurement (Table 5), IR spectrometry, Toxicity (Table 6) and Antimicrobial effectiveness (Table 7).

Such a final suspension with extracted silver nanoparticles could be concentrated to e.g. 18931 mg Ag/L by centrifugation at 11800 g.

3. Quantitative Enemy Dispersive X-Ray Analysis

Energy Dispersive X-Ray (EDX) analysis of bionanosilver or biocomponent, dried at 30° C., was performed with a FEI QUANTA 200F Scanning Electron Microscope with an EDX detector (EDAX Genesis 4000) and an EDX resolution of 129.68 eV, corresponding to an incident energy of 20.0 keV. Results are listed in Table 4.

4. (FT)IR Spectrometry

The (FT)IR spectrum of bionanosilver extracted from the *Lactobacillus* biocomponent, according to the present method. This bionanosilver originates from the outer cell compartments, i.e. glycocalyx, cell envelope and/or S-layer. The extracted bionanosilver associated with organic matter, stable in water at 3,000×g centrifugation, was analyzed by (FT)IR.

The absorption bands at 1601 cm$^{-1}$ and 1633 cm$^{-1}$ are characteristic of u(C=O) of an amino acid coordinated by a metal, for instance a metal bis(amino acid) complex such as trans-[Cu(gly)$_2$] at 1593 cm$^1$ or trans-[Pd(gly)$_2$] at 1642 cm$^{-1}$. The band at 1601 could also be attributed to an NH$_2$ bridging δ(NH$_2$) of such a metal bis(amino acid) complex. Metal complexes of amino acids are well known, and u(CO$_2$) of amino acid complexes are affected by coordination as well as by intermolecular interactions, since the coordinating C=O groups can be hydrogen bonded to the neighbouring molecule or weakly bonded to the metal of the neighbouring complex. The band at 1402 cm$^{-1}$ is characteristic for a u(C—O) of an amino acid COO group coordinated on a metal. Some of the vibration bands could exhibit a shift towards lower wavenumbers, potentially due to the negative charge of the bionanosilver at around neutral pH.

The presence of amino acids and proteins associated with extracted bionanosilver, possibly originating from the S-layer, the glycocalyx and also from glycoproteins or peptide residues from peptidoglycans, can also be concluded from the strong band at 1030 cm$^{-1}$, which is an aliphatic C—N stretching vibration band, and at 2922 cm$^{-1}$, the stretching vibration band for secondary amines.

These remaining peptides or amino acids are thought to exert a stabilizing effect on the silver particles and help determine the silver surface charge coupled to an isoelectric point at a higher pH, due to neutralisation of negatively charged glycocalyx material.

During the extraction step, 25% H$_2$SO$_4$ was used. The absence of SO$_4^{2-}$ in the final (washed) bionanosilver extracts was shown by Ion Chromatography analysis, but can also be concluded from the FT(IR) spectrum: there is no band at 1104 cm$^{-1}$ characteristic for SO$_4^{2-}$.

5. Transmission Electron Microscopy

In order to prepare thin sections for analysis by TEM, samples were fixed in 0.1 M of a cacaodylate buffer (pH 7.4) containing 2.5% glutaraldehyde and 2% formaldehyde, and embedded in 3% low melting agarose from Difco Laboratories (Detroit, Mich., USA). These samples were post-fixed in 1% osmium tetroxide. Between and after fixation steps, samples were washed with distilled water. Afterwards, samples were dehydrated in increasing concentrations of ethanol and, finally, in anhydrous propylene oxide. After embedding in Epon-Spurr medium, the specimen blocks were trimmed with a TM60 trimming unit (from Reichert-Jung A. G., Vienna, Austria) to obtain a cutting face of 0.5×1 mm$^2$-1×2 mm$^2$, and ultra-thin sections in the gold to mat silver interference colour range were cut using the Ultracut microtome from Reichert-Jung A. G. (Vienna, Austria). The sections were brought on pioloform and carbon coated copper grids (200 mesh). Once this was done, thin sections were stained with 2% uranyl acetate and then with lead citrate to determine the ultra-structure of the cells. Chemicals and grids were obtained from Agar Scientific (Stansted, United Kingdom). Imaging was performed with a EM208S transmission electron microscope (from FEI, Eindhoven, the Netherlands) operating at 80 kV.

For nanoparticles, samples were brought on home-made pioloform- and carbon-coated copper EM-grids. To increase hydrophilicity, the grids were pre-treated with Alcian-blue.

Samples were examined using a Technai 12 Spirit microscope (FEI) with Biotwin lense configuration at 120 kV and magnifications of 43 kx. Digital micrographs were made using the Bottom-mounted Eagle 4×4 K camera at magnifications of 49 kx. These were analysed using the Analysis 3.2 Pro software. A manual thresholding method was used. Particles were detected in a pre-defined frame excluding border particles and particles of less than 25 pixels. Frames in selected micrographs were analyzed resulting in >100 analyzed particles per sample. The mean diameter, area, sphericity, mean gray value, perimeter and convexity were determined for each particle.

6. Measurement of Zeta-Potential.

For 4 different samples a pH range was set up from 3-9. The samples of interest were:

(i) the *Lactobacillus fermentum* G2/10 biocomponent with nanosilver;

(ii) the nanoparticles extracted from the biocomponent according to the procedure detailed above, containing small silver nanoparticles between 0.9-7 nm;

(iii) the residual fraction of the biocomponent after extraction, containing larger silver particles between 20-200 nm; and iv) chemically prepared nanosilver.

The pH range was set up by using H$_2$SO$_4$ and NaOH at strong dilutions. In a second test range, a more narrow pH range was set up around the estimated iso-electric point. It was carefully determined that the difference in conductivity between samples was at most 1 log unit, always between 50 and 500 μS/cm. Dilutions were made in milliQ water. Tests were done to determine reproducibility, and the results were good (data not shown). The effect of dilution was also registered.

From the different samples, 5 ml was injected and electrophoretic mobility (μ) was measured at pH 3, 5, 7 and 9 respectively with a Malvern Zetasizer llc (Malvern, Worcestershire, United Kingdom) device at 25° C. and an applied electric field strength of 2000 V m$^{-1}$ using the Helmholtz-Smoluchouski equation:

$$\zeta = \frac{\mu \times \eta}{\varepsilon_0 \times \varepsilon_r}, \quad (1)$$

with μ being the electrophoretic mobility (m$^2$ s$^{-1}$ V$^{-1}$); $\varepsilon_0$ being the permittivity of vacuum (C$^2$ J$^{-1}$ m$^{-1}$); $\varepsilon_r$ being the dielectric constant; ζ being the ζ-potential (V); and η being the viscosity (kg m$^{-1}$ s$^{-1}$).

In a third test, the pH range was extended to below 3 for IEP determination of chemically prepared nanosilver.

A correction factor of 1.5 was applied when the particles were larger than 10 nm. The iso electric point was determined to be:

Chemically prepared nanosilver: 1.75

Nanosilver extracted from OCC: 4.1

Remaining biocomponent with larger nanoparticles: 5.3

7. UV-VIS Spectrometry

Surface plasmon resonance (SPR) is the frequency of oscillation of electrons in a conduction band, during the application of a changing electric field or electromagnetic radiation. Only metals with free electrons (Au, Ag, Cu and alkali earth metals) show SPR in the visible region, which results in intense colours. Next to particle shape and size, the refractive index of the medium as well as the average distance between neighboring silver nanoparticles influences the spectral properties. SPR of spherical particles in dilute dispersions is described by the Mie theory. For anisotropic particles, rather the Gans theory is used. Bigger particles induce a red shift to a higher wavelength and a somewhat broader SPR range. When the volume of silver nanoparticles is high, dipole interactions between neighboring particles occur and the Mie theory no longer applies. Stabilizers or surfactants influence the absorption spectra even when the size distribution of Ag and Au sols is the same.

Silver nanoparticles absorb in the visible area of the electromagnetic spectrum (380-450 nm) by plasmon resonance. This is the reason of the intensive yellow-brown color of silver nanoparticles.

The absorption spectra of UV and visible light were compared for different nanosilver preparations. Samples were diluted with distilled water to 40 mg Ag/L. Wavelength scans were taken by a Uvikon 932 spectrometer (from Kontron Instruments). The data range was 1 nm, scan range 20-800 nm and scan speed was 200 nm/minute. Quartz cuvettes were used to contain 1 mL samples.

The UV-VIS absorption spectra were analyzed for extracted bionanosilver (after washing), prepared according to the method detailed above, nanosilver on the G2/10 biocomponent, prepared according to (1), a commercial sample from Aqua Argentum and a dispersion of nanosilver of the prior art, which was found to agglomerate. All samples contained a silver concentration determined by ICP-MS of 40 mg Ag/L.

The absorption spectrum for the nanosilver on the biocomponent showed a broad absorption peak with a maximum absorption at 425 nm, and another absorption peak at 265 nm. The latter peak could be attributed to nucleic acids, proteins and various organic species present in the biocomponent.

The UV-VIS absorption spectrum of the extracted bionanosilver prepared as described above, showed a well-defined surface plasmon resonance band centered at 428 nm. This maximum was of a higher intensity than the 265 nm peak, indicative for the presence of various organic species at the surface that were relatively decreased when compared to the spectrum for the nanosilver on the biocomponent. The SPR peak did not tail as far as the SPR peak for nanosilver on the biocomponent, indicative for a more pure product with less aggregation.

Only a very low absorption was measured for 40 mg/L Ag in the Aqua Argentum sample. A maximum absorption was measured at 439 nm. The sample prepared according to the prior art did not show the typical UV-VIS absorption spectrum related to SPR. This was related to the agglomeration of the nanosilver into large aggregates. In the UV-VIS absorption spectrum of extracted bionanosilver, according to the method described in (2), but before the differential centrifugation step that washes out the fraction rich in associated organic material, a peak was observed with a maximum absorption at 212 nm, that was absent in all other spectra. This peak can be due to 4d10 and 4d9 S1 transition of $Ag^+$ ions. This data may be correlated to the high antimicrobial effectiveness of the extracted bionanosilver, since it is associated with an $Ag^+$ layer that results from $Ag^+$ dissolution from the $Ag^0$ nanoparticles.

8. X-Ray Diffraction Analysis

X-ray diffraction (XRD) of bionanosilver or biocomponent, dried at 30° C., was performed with a BRUKER D8 Discover. X-rays were generated by a copper X-ray tube with power 1.6 kW (40 kV, 40 mA). The wavelength CuKα corresponded to 1.54 Å. Measurements were made between 25 and 90 degrees 2-theta with a step time of 153.6 s and a step size of 0.02 degrees 2-theta. The XRD spectrum indicated the presence of pure elemental Ag(0).

9. Specific Surface Area

Bionanosilver or biocomponent samples were separated from a water dispersion by centrifugation and remaining water was removed by repeated washing and centrifugation steps with ethanol. The samples were then re-suspended in acetone. The samples were then transferred into calibrated glass recipients from the BET-A-MAT Areameter II of Juwe Laborgerate GmbH (Viersen, Germany). The samples inside the recipient were further dried at 90° C.

Once the samples were completely dry, they were saturated during 24 hours under $N_2$ gas flow. Before starting the measurements, the samples were cooled in a water bath for 20 minutes until room temperature was achieved. At the beginning of the measurements, recipients were submerged in liquid nitrogen during 3 minutes to desorb $N_2$ molecules at the particle surfaces. The overpressure thus generated was measured with a pressure manometer and converted to the specific surface area of the samples.

In Table 5, results are shown for the extracted bionanosilver, produced as described above, and for whole *Lactobacillus fermentum* G2/10 biocomponent with Ag-sorption according to the prior art. The extracted bionanosilver had a high specific surface area of 58.6 $m^2$/g. In literature, a specific surface area of 20 $m^2$/g is mentioned for nanosilver with particle sizes of about 30 nm. Interestingly, the surface area of the product according to the prior art protocol was around 20 $m^2$/g, and the nanoparticles formed around the biomass were about this size as observed by electron microscopy. Higher specific surface areas have been described for nanosilver, e.g. 158 $m^2$/g.

TABLE 5

Specific surface area determination by the Brunauer, Emmett, Teller (BET) $N_2$ gas adsorption isotherm method of bionanosilver produced by the present method, compared to nanosilver produced on *Lactobacillus fermentum* by Lin et al.(2005)

|  | Specific Surface Area (BET) |
|---|---|
| Extracted bionanosilver | 58.6 $m^2$/g |
| Nanosilver produced on *Lactobacillus fermentum* by the method from the prior art | 21.6 $m^2$/g |

10. Toxicity and Challenge Tests

In toxicity tests, concentrations of up to 15 mg/L bionanosilver (Ag) were found not to significantly alter the hatching, growth and development of *Artemia franciscana* into the mature stage. Thus, the MIC against *Artemia franciscana* was determined to be >15 mg/L (highest concentration tested, Table 6a).

TABLE 6a

Toxicity data expressed as Minimal Inhibitory Concentration (growth inhibition) of bionanosilver produced by the present method, against a Crustacean and a plant.

| | Organism tested | MIC |
|---|---|---|
| Crustacean | *Artemia franciscana* | >15 mg/L Ag |
| Plant | *Nicotiana tabacum* | >4 mg/L Ag |

To assess growth inhibition on *Nicotiana tabacum*, a sensitive dicotyl plant, the effect of different concentrations of bionanosilver in water used to irrigate the breeding grounds of tobacco plants was evaluated in terms of effect on seed germination, budding and plant growth. All experiments were set up in 4 replicates and were monitored during 5 weeks (25° C.). There was no effect on germination, budding, or size of the tobacco plant after 5 weeks for bionanosilver concentrations up to 4 mg/L (highest concentration tested). Thus, the MIC against *Nicotiana tabacum* was determined to be >4 mg/L (Table 6a).

Hence, an important asset of bionanosilver is its limited toxicity in ppm range against a Crustacean and a sensitive plant in short term toxicity tests.

In a further test, the capacity of bionanosilver to improve *Artemia franciscana* survival rates in a challenge with pathogenic *Vibrio campbellii* was investigated. For *Artemia franciscana* challenge tests, sterile artificial seawater (Instant Ocean, available from Aquarium systems USA) was prepared in milliQ water in an autoclave reactor. All treatments were set up in 20 mL aliquots of sterile artificial sea water contained within 50 mL Falcon tubes. Each treatment (performed in triplicate) consisted of 20 axenic *Artemia nauplii* in 20 mL artificial seawater, supplemented with a combination of $10^5$ CFU/ml (colony forming units) *Vibrio campbellii* LMG2163, and/or extracted bionanosilver as obtained from (2) at a final concentration of 20 mg Ag/L, or not supplemented and kept sterile in the control treatments (Table 6b).

TABLE 6b

Protection of *Artemia franciscana* from pathogenic *Vibrio campbelllii* by 20 mg/L bionanosilver (Ag) of this invention (mean +/− standard deviation of 3 replicates)

| Treatment | % survival Artemia franciscana |
|---|---|
| *Artemia franciscana* control | 73 ± 8 |
| *Artemia franciscana* + *V. campbellii* | 25 ± 9 |
| *Artemia franciscana* + *V. campbellii* + 20 mg Ag/L (bionanosilver) | 67 ± 19 |

It was found that mortality rates of up to 75% on average were obtained in the treatments with the *Artemia franciscana* pathogen *Vibrio campbellii* LMG2163, which was significantly higher than mortality in the control treatments (25%). By supplementing with 20 mg/L bionanosilver (Ag), mortality significantly ($P<0.05$) decreased from 75% on average to 33%.

11. Minimal Inhibitory Concentration.

For the determination of the minimal inhibitory concentration (MIC) of nanosilver against different bacteria and fungi, i.e. the lowest concentration at which these micro-organisms show an inhibition of growth, the following protocol was used:

Journal of Antimicrobial Chemotherapy Supplement (JAC [2001] 48, Suppl. S1), March 2006, Chapter 2: Determination of minimal inhibitory concentrations; Macrodilution method.

Cultures of *Staphylococcus aureus*, *Pseudomonas aeruginosa* and *Candida albicans* were grown overnight and diluted to $150 \times 10^6$ bacterial cells or $5 \times 10^6$ yeast cells per mL (according to an optical density measured at 610 nm). These stock solutions were further diluted 500 times, in steps of 1 to 10 and 1 to 5. The final culture was then two times diluted in the final microtiter plate, resulting in a final dilution of 1:1000.

The test compound was diluted into the microtiter cultures at a concentration range from 0.5 to 470 mg/L Ag. The microtiter plates were then incubated at 30° C. on a shaker. After 24 h the plates were taken out of the incubation oven and growth was compared with the control row, both visually and by OD measurement at 610 nm.

For *Aspergillus niger*, a culture on MEA agar plate of at least 1 week old was harvested as follows. To harvest the black spores, 10 mL of a 0.05% Tween 80 solution in water was poured over the plate and carefully the spores were mixed into the sterile water with a sterile spatulum. In order to remove the mycelia from the spores, the black suspension was pipetted into a sterile Erlenmeyer filled with glass pearls, and vortexed during one minute. The final suspension was filtered over a 50 μm cutoff sterile filter. Microscopic analysis was done to verify that all mycelia had been removed. The optical density of the spore culture was measured at 610 nm and diluted to $5 \times 10^6$ spores. This suspension was in turn diluted 50 times. The final culture was then again diluted twice in the final microtiter plate, resulting in a final dilution of 1:100.

The algicidal properties of bionanosilver were determined as follows. Test tubes containing 10 mL BG11 medium (Stanier et al., 1971) were inoculated with 0.5 mL of an actively growing liquid BG11 culture of *Chlorella vulgaris* and incubated at 20° C., 65% relative humidity and 1000 Lux (16 hours/day). Growth was evaluated after 2 weeks by spectrophotometric measurement. Different concentrations of the bionanosilver formulation, ranging from 20 mg Ag/L to 0.01 mg Ag/L, were tested by dosage in the test tubes. The MIC value is the lowest test concentration at which complete inhibition of organism growth was observed. The MIC value of the bionanosilver product is shown in Table 7a.

TABLE 7a

Minimal Inhibitory Concentration (MIC) against several bacteria, yeast and mold, for different fractions of bionanosilver produced by the present method, compared to chemically prepared nanosilver by the method of the prior art, silver nitrate, and data found in literature.

| | Bacteria | | Fungi | | |
|---|---|---|---|---|---|
| | Gram negative *Pseudomonas aeruginosa* | Gram positive *staphylococcus aureus* | yeast *Candida albicans* | mold *Aspergillus niger* | Algae *Chlorella vulgaris* |
| extracted bionanosilver | 4.3 | 17.3 | 10 | 4.3 | 0.1 |
| residual bionanosilver (after extraction) | 7.4 | 14.8 | 14.8 | 7.4 | n.d. |
| bionanosilver on biocomponent (before extraction) | 5.5 | 20.2 | 20.2 | 10.1 | 0.13 |
| chemically prepared nanosilver according to prior art | 100 | 100 | 100 | >400 | n.d. |
| nanosilver composite with porous matrix (Zeng et al. 2007) | n.a. | n.a. | 28.1 | n.a. | n.a. |
| colloidal silver stabilized with sodium | n.a. | n.a. | 64.3 | n.a. | n.a. |

TABLE 7a-continued

Minimal Inhibitory Concentration (MIC) against several bacteria, yeast and mold, for different fractions of bionanosilver produced by the present method, compared to chemically prepared nanosilver by the method of the prior art, silver nitrate, and data found in literature.

| | Bacteria | | Fungi | | |
|---|---|---|---|---|---|
| | Gram negative *Pseudomonas aeruginosa* | Gram positive *staphylococcus aureus* | yeast *Candida albicans* | mold *Aspergillus niger* | Algae *Chlorella vulgaris* |
| oleate (Zeng et al. 2007) | | | | | |
| nanosilver (Morones et al. 2005) | 75 | n.a. | n.a. | n.a. | n.a. |
| silver nitrate | 6.3 | 12.5 | 12.5 | 25 | n.a. | n.d. = not determined;
n.a. = not available

In total, 5 different silver-based compounds were tested and compared. Three different fractions of nanosilver obtained with the present method were compared:
  i) nanosilver on the biocomponent, before extraction
  ii) nanosilver extracted from the biocomponent (containing 0.9-7 nm particles)
  iii) residual biocomponent after extraction, containing larger silver particles 20-200 nm These three fractions were compared to chemically prepared nanosilver with the method of the prior art, and to silver nitrate. The nanosilver prepared according to the prior art was found to be highly susceptible to agglomeration.

Results for MIC tests, compared to values found in literature, are listed in Table 7a.

The MIC value of nanosilver prepared by the method of the prior art with the G2/10 strain, were found to be not significantly different from the MIC values for silver nitrate (results not shown). This agrees with the XRD analysis, Electron Microscopy and EDX analysis on this product, indicating that only a small fraction of the $Ag^+$ had been effectively converted to $Ag^0$, and was thus comparable to the activity of $Ag^+$ from $AgNO_3$.

From the results in Table 7a, the following conclusions can be drawn:
The extracted nanosilver is more reactive than the nanosilver on the biocomponent (before extraction): MIC values are more than 2 times lower against Fungi. The extracted nanosilver is more reactive than silver nitrate against *P. aeruginosa*, *C. albicans*, *A. niger*, but less reactive than $AgNO_3$ against *S. aureus*. The nanosilver prepared according to the prior art showed very little antimicrobial activity, which could be due to agglomeration. The residual biocomponent after extraction, containing silver nanoparticles >20 nm, was still very effective against microorganisms, although less effective than the smaller nanosilver obtained from the first extraction step.

The problem often encountered with the antimicrobial action of nanosilver and silver-based actives in general, is the compromised antimicrobial efficacy against Fungi, which is often far less than the antibacterial efficacy. This results in higher doses of silver necessary for an antifungal effect against yeasts or molds than those necessary for an antibacterial effect. Since often both effects are required at the same time, the overall silver dosage is determined by the limiting efficacy against Fungi. This effect was also observed with the nanosilver obtained by the method from the prior art, where the MIC against *Aspergillus niger* was more than 400 mg Ag/L. From the results in Table 7a, it can be observed that the extracted bionanosilver is as effective against the mold *Aspergillus niger* than it is against the Gram negative bacterium *Pseudomonas aeruginosa*, both with an MIC of 4.3 mg Ag/L, whereas the efficicacy against the yeast *Candida albicans* was better than the efficacy against the Gram positive bacterium *Staphycococcus aureus*, with MIC values of 10 and 17.3 mg Ag/L respectively.

12. Test with Zeolite

A problem commonly encountered in the field, and especially in the use of silver-based actives as formulated biocides in plastics, polymers, sealants, textile fibers, or paints, is the depletion of $Ag^+$ from the formulation. This is especially true with $Ag^+$ based ion exchange carriers, minerals or resins, for example $Ag^+$ zeolites commercially available at a broad range of $Ag^+$ concentrations. The result of fast depletion of $Ag^+$ from the formulation is loss of the antimicrobial effect of the formulation and release of insufficient $Ag^+$ for total destruction of microbiota, which may contribute to build-up of $Ag^+$ resistance. This is especially the case when a solvent with high cationic strength is passed over the formulation, where $Ag^+$ is exchanged from the resin or carrier for cations present in high concentrations. Typical examples would include antimicrobial paint to prevent bio-deterioration or bio-fouling exposed to salt water, for instance sea water. Another example would be the exposure of an antimicrobial textile fiber exposed to human sweat for a long period of time. In such cases, the $Ag^+$ formulation would quickly be depleted of $Ag^+$. A more controlled release of $Ag^+$ could be maintained by using silver nanoparticles. The concept of combining the bionanosilver obtained by the present method with zeolite was studied in detail. The bionanosilver with specific surface characteristics indicated by zeta-potential measurements, specific surface area, EDX, F(FT)IR and electron microscopy (TEM), and with good antimicrobial properties against Fungi, bacteria and algae, was coated onto Zeolith N (Zeolite Aluminium silicate, Evers E. K., Hopsten, Germany). This was achieved by mixing 20 mL of a bionanosilver dispersion of 10,385 mg Ag/L in water with 10 g Zeolith N for about 30 minutes and drying the resulting suspension in an oven at 105° C. The resulting zeolite powder was homogeneously light grey in color and the bionanosilver could not be removed from the zeolite matrix by washing with water. The zeolite contained 2% Ag by weight.

In order to test the effect of water with high cationic strength on Ag depletion from the zeolite matrix, 1 volume of bionanosilver zeolite was washed with 10 volumes of sterile artificial seawater (Instant Ocean, available from Aquarium systems USA) by shaking at 28° C. The washing water was refreshed every 24 hours, by centrifugation and resuspension of the bionanosilver zeolite. The same test was repeated for commercial Ag⁺-zeolite combination from Sanitized AG containing 2% Ag⁺ by weight.

The MIC values against a Fungus, *Aspergillus niger*, were determined before and after washing with artificial seawater. The MIC value for the Sanitized Ag⁺ zeolite was found to increase during the several washing steps, whereas the MIC value for the bionanosilver zeolite remained almost identical. Results after 72 h of exposure to salt water are shown in Table 7b. These results indicate that the antimicrobial action of bionanosilver sustains better the effect of exposure to high salt concentrations, when anchored to a porous carrier like zeolite, due to the more controlled release of Ag⁺ and the less stringent effect of ion exchange under these conditions, when compared to the Ag⁺ zeolite ion exchange system.

TABLE 7b

Comparison between the MIC obtained from a bionanosilver on zeolite of this invention compared to ionic Ag⁺-zeolite (from Sanitized AG, Switzerland) at the same Ag loading of 2% (w/w), before and after exposure to sterile artificial sea water (Instant Ocean, available from Aquarium Systems USA).

|  | mold *Aspergillus niger* |
|---|---|
| Extracted bionanosilver on zeolite (2% Ag w/w) | 3.1 |
| Sanitized BAC silver zeolite (2% Ag⁺ w/w) | 3.1 |
| Extracted bionanosilver on zeolite (2% Ag w/w) after 72 hours in sterile sea water | 3.3 |
| Sanitized BAC silver zeolite (2% Ag⁺ w/w) after 72 hours in sterile sea water | 6.6 |

13. Test with Polymer

Bionanosilver obtained by the method of the invention described above was dispersed into the aqueous-based acrylic ester polymer Rhodopas Ultrafine PR3500 (Rhodia, Aubervilliers, France) at concentrations of 100 mg/kg and 1000 mg/kg respectively. The polymer with nanosilver was coated on macroporous polypropylene fiber pads of 5 mm thick by dipping the pads into the polymer solution for 5 seconds, and further drying in an oven at 100° C. during 24 hours.

Since contamination of soft drinks due to bio-films growing inside automated reservoirs (e.g. in restaurants) is a recurrent practical issue, microbial contamination on the pads by daily irrigation with soft drink was compared between treated and untreated pads.

The treated and untreated polypropylene pads were glued into small plastic funnels, connected to a 1 L soft drink reservoir by plastic tubings with 10 mm internal diameter. Daily, 100 mL soft drink was passed over the polypropylene pads, followed by 100 mL tap water. From day 2 onward, samples of 10 mL water were collected and a dilution series was plated on Trypticase Soy Agar plates, for total microbial count determination. The results are listed in Table 8.

TABLE 8

Effect of bionanosilver mixed at different concentrations in the polymer RHODOPAS PR 3500 (Rhodia, France) on microbial loadings measured on polypropylene fiber pads treated with PR3500, upon irrigation by soft drink.

|  | Bionanosilver at 1000 mg Ag kg⁻¹ PR3500 CFU ml⁻¹ | Bionanosilver at 100 mg Ag kg-1 PR3500 CFU ml⁻¹ | Control (PR3500 without Ag) CFU ml⁻¹ |
|---|---|---|---|
| Day 1 | 0 | 0 | 7 |
| Day 2 | 0 | 0 | 362 |
| Day 3 | 0 | 0 | 124 |
| Day 4 | 0 | 0 | 184 |
| Day 5 | 0 | 42 | 103 |
| Day 6 | 4 | 207 | 356 |
| Day 7 | 4 | 800 | 265 |

From the results, it can be concluded that no biofilm formation occurred on the polypropylene pads coated with 1000 ppm bionanosilver (Ag), whereas the non-treated pads were a source of bacterial contamination of the soft drink. The pads coated with 100 ppm Ag were microbially fouled in the same manner as the untreated control pads within 1 week, although they had remained sterile during at least 4 days. This is an indication that bionanosilver may prevent bio-film formation even in eutrophic environments, thus increasing hygiene on surfaces and applications. Moreover, the results demonstrate that the bionanosilver remains anti-microbially active in the acrylic ester polymer.

14. Effect of Treatment of the Biocomponent with Low Concentrations of HCl while Heating In order to evaluate the effect of acidic thermolysis on the biocomponent (after cultivation) on the conversion efficacy of $Ag^+$ to $Ag^0$, 5 grams of G2/10 dry weight was treated with 0.1 N HCl at 60° C. during 5 minutes. The biocomponent was then centrifuged at 5000×g, washed with deionized water, and post-saponified as well as treated for $Ag^0$ production as described in (1).

The $Ag^+$ to $Ag^0$ conversion efficacy thus obtained, was compared with the procedure containing the same biocomponent and carried out under identical conditions, but without treatment of the biocomponent with 0.1 N HCl at 60° C.

The $Ag^0$ conversion efficacy was determined by measuring residual $Ag^+$ in solution in the reaction mixtures.

It was found that from the concentration of 1000 mg $Ag^+$/L that was dosed in each of the reactions, after the $Ag^0$ production process according to the present method, there was 138 mg $Ag^+$/L less remaining in solution in the reaction mixture when the biocomponent has been treated with 0.1 N HCl at 60° C., when compared to the reaction without the acidic thermolysis step. This indicates a higher $Ag^+$ to $Ag^0$ conversion efficacy when the biocomponent is treated by a mild acidic thermolysis step prior to saponification.

The invention claimed is:

1. A method for producing atomic silver ($Ag^0$) nanoparticles associated with 20 to 80% by weight of a biocomponent of the genus *Lactobacillus*, said method comprising the step of incubating bacteria of the genus *Lactobacillus* for about 30 minutes to about 16 hours with an aqueous solution comprising at least 4 mM of a silver salt in the presence of ammonia and an alkali metal hydroxide until a biomass of bacteria containing atomic $Ag^0$ silver nanoparticles is formed.

2. A method for producing atomic silver nanoparticles associated with 20 to 80% by weight of a biocomponent of the genus *Lactobacillus*, said method comprising the steps of:
   (a) incubating bacteria of the genus *Lactobacillus* for about 30 minutes to about 16 hours with an aqueous solution comprising at least 4 mM of a silver salt in the presence of ammonia and an alkali metal hydroxide until a biomass of bacteria containing atomic Ag⁰ silver nanoparticles is formed; and (b) extracting said atomic Ag⁰ silver nanoparticles from said biomass by means of concentrated alkali metal hydroxide or concentrated inorganic acid or enzymes.

3. The method according to claim 1, wherein the bacteria used for the incubation step have been pre-treated for increasing the sugar-rich structures in their cell envelope.

4. The method according to claim 1, wherein the bacteria used for the incubation step have been pre-treated by fermentation under a carbon/nitrogen ratio of at least 10:1.

5. The method according to claim 1, wherein the bacteria used for the incubation step have been pre-treated by fermentation in the presence of a fermentable sugar at a concentration of at least 20 g/L.

6. The method according to claim 1, wherein the bacteria used for the incubation step have been pre-treated by fermentation until their dry weight is increased by at least 200%.

7. The method according to claim 1, wherein the bacteria used for the incubation step have been pre-treated by fermentation during at least 10 hours.

8. The method according to claim 1, wherein the bacteria used for the incubation step have been pre-treated by fermentation at a temperature within a range from 4° C. to 40° C.

9. The method according to claim 1, wherein the bacteria used for the incubation step have been pre-treated by acidic hydrolysis of glycocalyx, cell envelope and/or S-layer.

10. The method according to claim 1, wherein the bacteria used for the incubation step have been pre-treated by acidic hydrolysis at a temperature above 35° C.

11. The method according to claim 2, wherein the extraction step is performed during at least 5 minutes.

12. The method according to claim 2, wherein said concentrated alkali metal hydroxide is sodium hydroxide 0.01 N-2.0 N and wherein the extraction step (b) is performed at a temperature of at least 70° C.

13. The method according to claim 2, wherein said concentrated inorganic strong acid is sulphuric acid 1N-10N and wherein the extraction step is performed at a temperature of at least 0° C.

14. The method according to claim 2, wherein the extraction step is performed at a temperature not above 100° C.

15. The method according to claim 1, wherein the incubation step is performed at a temperature from 10° C. to 40° C.

16. The method according to claim 1, wherein the incubation step is performed in the absence of an externally added reducing agent or a capping agent (such as a surfactant).

17. The method according to claim 2, wherein the extraction step further comprises centrifugation or filtration of a slurry of said extracted atomic Ag⁰ silver nanoparticles.

18. The method according to claim 2, wherein the extraction step produces (i) a first fraction of atomic silver nanoparticles with an average particle size from 1 to 8 nm and being associated with the cell envelope or glycocalyx and/or S-layer of said bacteria and (ii) a second fraction of atomic silver nanoparticles with an average particle size from 20 to 200 nm and being associated with the cytoplasm of said bacteria.

19. The method according to claim 18, further comprising the step of separating said first fraction (i) from said second fraction (ii).

20. The method according to claim 18, wherein the weight ratio of said first fraction (i) to said second fraction (ii) is higher than 1:1.

21. The method according to claim 18, wherein said second fraction (ii) is introduced as a component of a conductive ink or a catalyst.

22. The method according to claim 18, wherein said first fraction (i) and/or said second fraction (ii) is introduced as a component of an anti-microbial composition.

23. The method according to claim 1, wherein said atomic silver nanoparticles exhibit a ratio of the average particle size to the specific surface area (BET) of from 0.015 to 0.15 nm/m2/g.

24. The method according to claim 2, wherein said silver nanoparticles exhibit a ratio of the average particle size to the specific surface area (BET) of from 0.015 to 0.15 nm/m2/g.

25. The method according to claim 1, wherein the bacteria used for the incubation step have been pre-treated by fermentation in the presence of a fermentable sugar at a concentration of more than 50 g/L.

26. The method according to claim 2, wherein said concentrated alkali metal hydroxide is sodium hydroxide 0.5 N-2.0 N and wherein the extraction step (b) is performed at a temperature of at least 70° C.

* * * * *